(12) United States Patent
Papac et al.

(10) Patent No.: US 8,371,695 B2
(45) Date of Patent: Feb. 12, 2013

(54) REAL-TIME SPECTRALLY-ADJUSTABLE OPHTHALMIC ILLUMINATION

(75) Inventors: Michael Papac, Tustin, CA (US);
Ronald T. Smith, Irvine, CA (US);
Michael J. Yadlowsky, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 104 days.

(21) Appl. No.: 13/076,639

(22) Filed: Mar. 31, 2011

(65) Prior Publication Data

US 2011/0292344 A1 Dec. 1, 2011

Related U.S. Application Data

(60) Provisional application No. 61/349,287, filed on May 28, 2010.

(51) Int. Cl.
*A61B 3/10* (2006.01)
*A61B 18/18* (2006.01)
*A61N 5/06* (2006.01)
*A61N 1/30* (2006.01)

(52) U.S. Cl. ............... 351/221; 351/205; 606/4; 607/88; 604/21

(58) Field of Classification Search .................. 351/221, 351/200, 205, 213; 606/2–19; 128/898; 362/572; 607/88–95; 600/156–183; 604/4, 604/21
See application file for complete search history.

(56) References Cited

U.S. PATENT DOCUMENTS

| | | | |
|---|---|---|---|
| 6,183,086 B1 * | 2/2001 | Neubert | 351/221 |
| 6,917,057 B2 | 7/2005 | Stokes et al. | |
| 7,682,027 B2 | 3/2010 | Buczek et al. | |
| 2005/0213092 A1 * | 9/2005 | MacKinnon et al. | 356/336 |
| 2006/0146340 A1 * | 7/2006 | Szwaykowski et al. | 356/495 |
| 2008/0246920 A1 * | 10/2008 | Buczek et al. | 351/221 |
| 2008/0269728 A1 * | 10/2008 | Buczek et al. | 606/4 |
| 2010/0177280 A1 | 7/2010 | Buczek et al. | |

OTHER PUBLICATIONS

Papac, et al.; U.S. Appl. No. 13/076,570, filed Mar. 31, 2011; currently pending; Bibliographic Data Only.

* cited by examiner

*Primary Examiner* — Dawayne A Pinkney
(74) *Attorney, Agent, or Firm* — Keiko Ichiye

(57) ABSTRACT

An ophthalmic illuminator is provided that includes a plurality of color sources, each color source producing a light of a corresponding color; a combiner for combining the light from the color sources to produced a combined light; at least one optical fiber configured to receive the combined light and propagate the received combined light towards a distal end of the ophthalmic illuminator; and a controller configured to control an intensity for each of the color sources responsive to a sampling of a spectral content for the combined light.

19 Claims, 4 Drawing Sheets

REAL-TIME SPECTRALLY-ADJUSTABLE OPHTHALMIC ILLUMINATION

This application claims priority to U.S. Provisional Patent Application Ser. No. 61/349,287 filed on May 28, 2010.

TECHNICAL FIELD

This application relates to illumination in ophthalmic procedures and more particularly to ophthalmic illumination with spectral adjustment.

BACKGROUND

Ophthalmic illuminators allow a surgeon to illuminate the interior structure of the eye such as the vitreous and the retina during surgical procedures. For example, an endoscopic ophthalmic illuminator (endo-illuminator) includes an optical fiber within the bore of a cannula. By driving a proximal end of the optical fiber with a suitable light source, light emitted from a distal end of the fiber illuminates the desired portion of the eye during a surgical procedure. Alternatively, a physician may illuminate the eye with fiber optic illumination while using an ophthalmic microscope.

One factor for ophthalmic illumination is the spectral output. In general, biological tissue is a broadband reflector such that white light illumination is preferable. However, there are situations such as the use of dyes or the detection of certain proteins in which a physician will prefer a suitably colored illumination. In general, most conventional white light sources such as a white light LED provide a fixed spectral output. However, the desired spectral output for ophthalmic illumination may vary depending upon numerous factors that are difficult to predict a priori such as: the physical appearance of the retina; the desired illuminance (luminous flux/area) in the operating field, the desired Color Rending Index (CRI) for adequate visualization of the retinal tissue; and the degree of contrast enhancement or color suppression desired during the surgery; Another factor for ophthalmic illumination is the resulting aphakic hazard potential, which is the potential for light-induced photochemical damage to the retina. In general, there is virtually no aphakic hazard at wavelengths longer than 510 nm. The aphakic hazard can thus be virtually eliminated by using only those wavelengths longer than 510 nm. Thus, the desired spectral output for ophthalmic illumination may also vary according to the expected length of the operation and the proximity of the distal end of the illumination probe to the retina.

Accordingly, there is a need in the art for an improved ophthalmic illuminator that adjusts its output spectrum in real time.

SUMMARY

In accordance with a first aspect of the disclosure, an ophthalmic illuminator is provided that includes: a plurality of color sources, each color source producing a light of a corresponding color; a combiner for combining the light from the color sources to produced a combined light; at least one optical fiber configured to receive the combined light and propagate the received combined light towards a distal end of the ophthalmic illuminator; and a controller for controlling an intensity for each of the color sources responsive to a sampling of a spectral content for the combined light.

In accordance with a second aspect of the invention, a method of controlling an ophthalmic illumination is provided that includes: producing a plurality of lights of different colors; combining the plurality of lights of different colors to produce a combined light; illuminating an operating field within a human eye with the combined light; measuring a spectral radiometric function for the combined light during the illumination; and responsive to the measurement, adjusting an intensity for at least one of the lights of different colors.

In accordance with a third aspect of the invention, an ophthalmic illuminator is provided that includes: a red LED; a green LED; a blue LED; a combiner for combining light from the LEDs to produce a combined light; at least one optical fiber configured to receive the combined light and propagate the received combined light towards a distal end of the ophthalmic illuminator; and a controller configured to control an intensity for each of LEDs responsive to a sampling of a spectral content for the combined light.

DESCRIPTION OF FIGURES

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
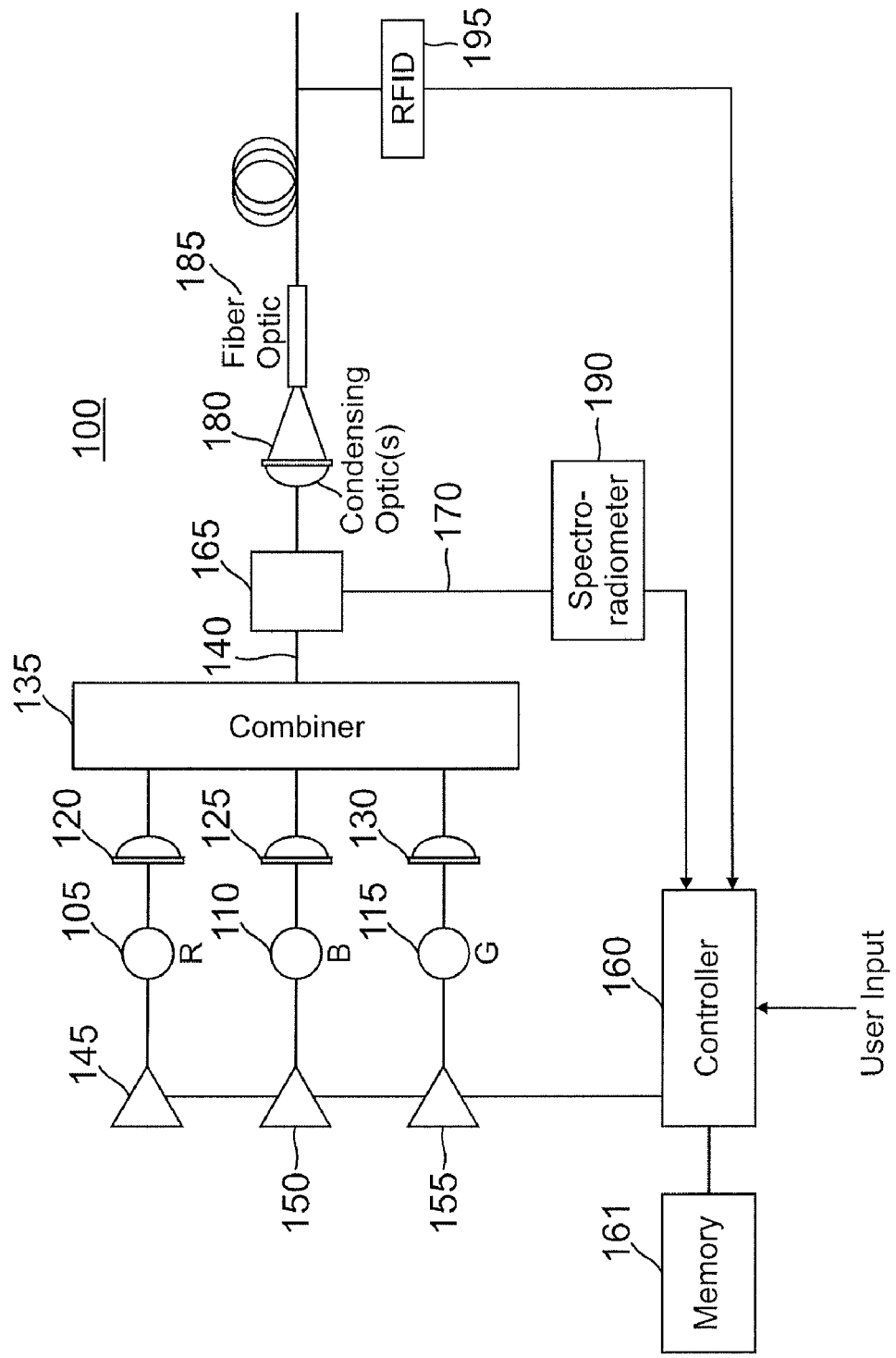
FIG. 1 illustrates a spectrally-adjustable ophthalmic fiber illumination probe.

To provide spectral output selectivity and brightness flexibility, a plurality of color light sources are selectively combined to produce an illuminating light having a desired spectral output. In this fashion, a clinician may thus not only alter the spectral output for the illumination but also vary (or keep constant) the resulting luminous flux despite the spectral augmentation. Turning now to the drawings, FIG. 1 illustrates a spectrally-adjustable ophthalmic illuminator probe 100. Illuminator 100 includes a red LED source 105, a blue LED source 110 and a green LED source 115. Each LED associates with a corresponding collimating lens. Thus, red light from red (R) LED source 105 is collimated through a lens 120, blue light from blue (B) LED source 110 is collimated through a lens 125, and green light from green (G) LED source 115 is collimated through a lens 130. The resulting collimated light beams are received at a combiner 135 to produce a combined light beam 140. Combiner 135 may comprise a Phillips prism, a dichroic cube, or other suitable optical combiner.

Because of the RGB contribution from the sources, combined light beam 140 may nominally be a white light beam. To provide spectral variability in addition to white light illumination, the radiant flux (intensity) for each light source may be tuned as desired. For example, a variable current amplifier 145 may vary the radiant flux produced by red LED source 105, a variable current amplifier 150 may vary the radiant flux from blue LED source 110, and a variable current amplifier 155 may vary the radian flux for green LED source 115. Other techniques may also be used to vary or tune the light intensity from each source. For example, constant power sources may drive the LEDs through pulse width modulators. A controller 160 such as a microprocessor or microcontroller controls the radiant flux from each light source accordingly. Thus, for illuminator 100, controller 160 controls the amount of gain applied by each current amplifier.

In one embodiment, controller 160 automatically adjusts the gain responsive to feedback as sensed through an optical sampler 165 that samples combined beam 140. For example, optical sampler 165 may comprise a beam splitter or a folding mirror to split off a relatively small portion of the combined beam 140 as a sampled beam 170. To analyze the spectral content of the sampled beam 170 (and thus of combined beam 140), controller receives data from a spectroradiometer 190 that receives sampled beam 170.

The remaining unsampled portion of combined beam 140 is received by a condensing optic lens 180 so as to couple into an optic fiber 185 (or optic fiber bundle). Fiber 185 may thus be the illumination source in ophthalmic instruments such as an ophthalmic microscope, slit lamps, indirect ophthalmoscopes, and fiber endo-illuminators. Controller 160 is also responsive to user input such that a physician may manually command the appropriate gains so as to achieve the desired spectral content for combined beam 140.

In that regard, the general desire for white vitreoretinal illumination flows from the phenomenon of color rendering, which is the ability of the illuminating light to render the appearance of various colors as they should appear to the human observer. To help indicate how colors will appear under spectrally-different light sources, a color rendering index (CRI) has been derived as known in the optic arts. In general, the more spectrally broadband a source is, the higher its CRI value will be. White light illumination thus has a high CRI value. But as the illumination takes on color, the CRI index will drop. For example, illumination at wavelengths only of 510 nm in wavelength or longer will have a relatively low CRI. As will be discussed further herein, controller 160 may automatically control the CRI by adjusting the radiant flux from each source to achieve a desired chromaticity value as defined by, for example, the International Commission on Illumination (CIE) 1931 color space.

The automatic control provided by controller 160 in response to sensing the spectral content of the combined light advantageously minimizes or eliminates aphakic hazard in certain embodiments. In that regard, stringent guidelines on total aphakic exposure such as 10 J/cm$^2$ may be satisfied, thereby increasing patient safety. For controller 160 to properly calculate the total aphakic irradiance, a correlation between the irradiance at the retina and the radiant flux measured by spectroradiometer 190 of sampled beam 170 is useful. The irradiance on the retina depends upon a number of factors such as the separation between an emitting distal end of a probe holding fiber 185 and the retina. As the distal end of the probe moves closer to the retina, the more intense will be the retinal irradiance will increase. A typical separation between the probe and the retina for conventional endo-illuminators is 5 to 15 mm. However, for a laser probe such as used in retinal photocoagulation therapy, the separation may be in the range of 2 to 4 mm. Another factor affecting time-averaged retinal irradiance is whether the illumination probe is pointed at the same area of the retina as opposed to sequentially moving the illumination to different portions of the retina. Other factors include the spread angle of the emitted light beam, the incident angle for the emitted light beam onto the retina, and the detailed structure and physical condition of the retina as well as obscuring effects of other tissues such as vitreous and epiretinal membranes.

To assist controller 160 in making an a priori estimate of the expected irradiance, illumination probe 100 may include an RFID tag 195 so that an RFID interrogator (not illustrated) may read associated RFID data from tag 195 and provide the data to controller 160. For example, an estimate of expected conditions and beam spread angle associated with a given probe is loaded onto tag 195 so that controller 160 can correlate between spectral power measurements of sampled beam 170 and a corresponding irradiance at the retina.

Figure 2:
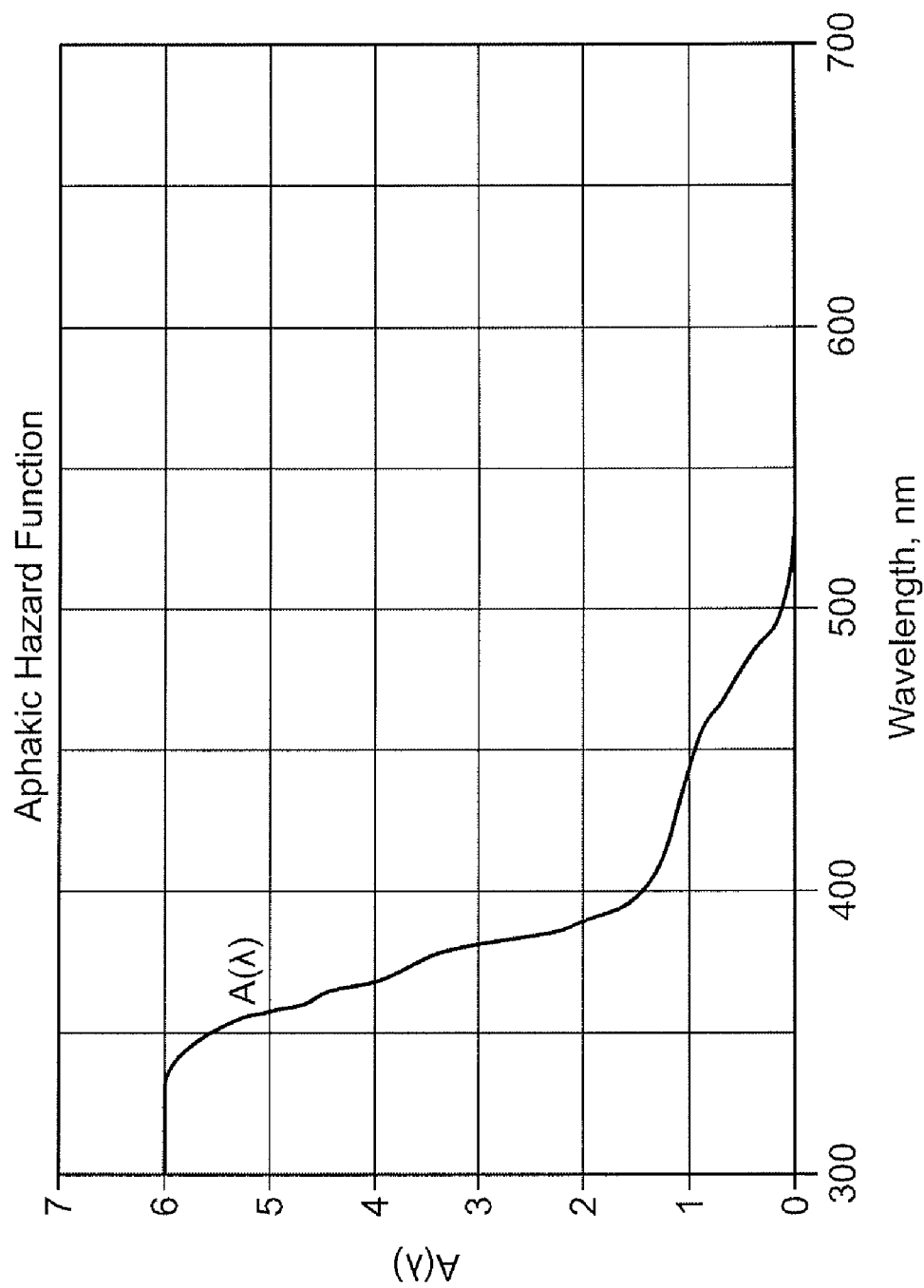
FIG. 2 is a graph of the aphakic hazard function.

Spectroradiometer 190 may sample the entire visible spectrum for sampled beam 170 or merely sample the spectral power at selected wavelengths having the expected predominant optical energy. Having determined some suitable radiometric measure (denoted as R) such as radiometric flux or irradiance at the sampled wavelengths, controller 160 may thus construct a corresponding spectral radiometric function R'($\lambda$). e.g. watts/nm. An accurate measure of the aphakic hazard requires a translation of such a radiometric quantity to an aphakic radiometric quantity such as aphakic irradiance or aphakic radiometric power. To calculate an aphakic radiometric quantity, controller 160 retrieves the aphakic hazard function A($\lambda$) as illustrated in FIG. 2 from a memory 161. Controller 160 then numerically integrates according to the following equation:

$$R_{aph} = \int R'(\lambda) A(\lambda) d\lambda$$

where $R_{aph}$ is an aphakically weighted radiometric quantity as determined by the type of radiometric quantity (radiometric flux, irradiance, etc.) used to establish R'($\lambda$). Controller 160 may then determine the total aphakic exposure over the procedure time by multiplying $R_{aph}$ by the retinal illumination duration. Should controller 160 determine that the aphakic exposure has exceeded some maximum threshold such as 10 J/cm$^2$, controller 160 may then reduce or eliminate the emission from any color light source having wavelengths less than 510 nm.

Figure 3:
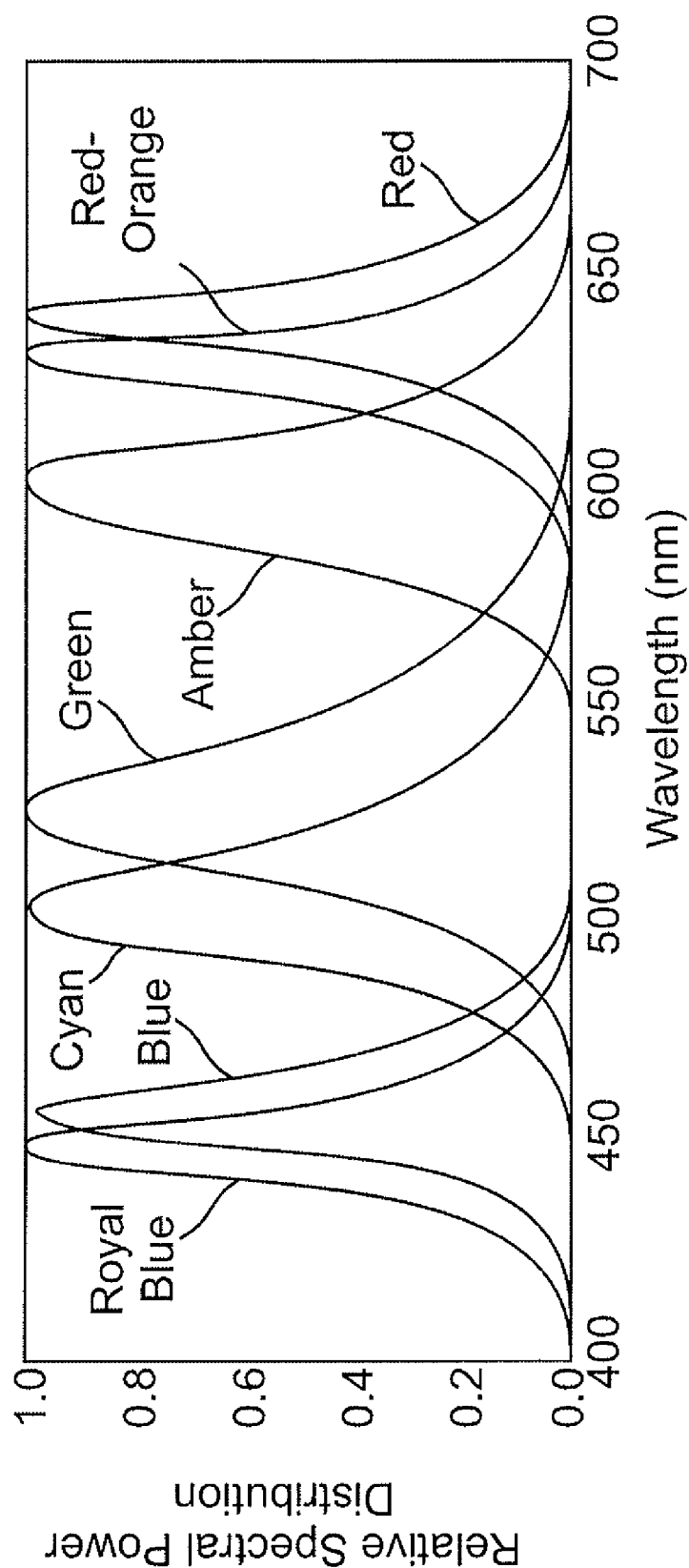
FIG. 3 illustrates the spectral power distribution bands for various color LED sources.

Another consideration besides the aphakic hazard that controller 160 may address is contrast, which is typically defined as the luminance ratio between the brightest and dimmest portions of the retinal image. Whether a particular retinal tissue reflects strongly or weakly depends on its reflectance spectrum multiplied by the illumination spectrum as integrated over the visible wavelengths. If a particular retinal tissue is highly absorptive over a spectral region corresponding to one of the color sources but a different retinal tissue is highly reflective at that same wavelength, controller 160 could increase the contrast between the two retinal tissues by suppressing the remaining color sources. Alternatively, there may be high contrast in the presence of white light (full spectrum) illumination such that controller 160 tunes the color sources to effect white light illumination. Conversely, low contrast may be achieved with single color source illumination. Depending upon the circumstances of a particular therapy, either contrast enhancement or suppression may be desirable. The degree of suppression or enhancement depends upon the spectral behavior for the various light sources and the spectral reflectance characteristics of the tissue being observed. As seen in FIG. 3, which illustrates the spectra for various commercially-available LED color sources, these sources typically have relatively narrow spectral bandwidths. Such narrowband emission enhances the ability to increase or suppress contrast as desired by controller 160.

Figure 4:
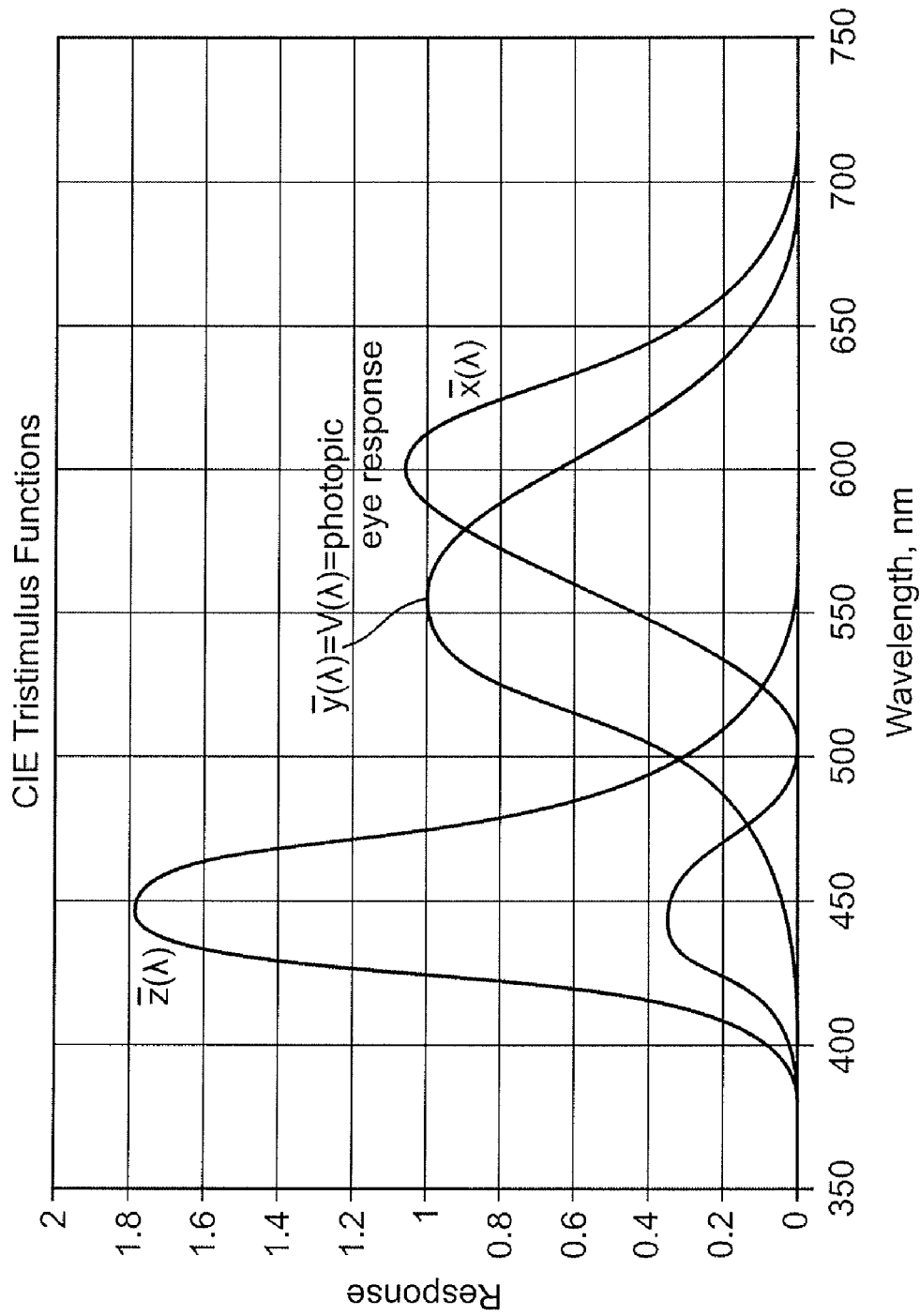
FIG. 4 is a graph of the CIE tristimulus functions.

To achieve a particular chromaticity, controller 160 may be configured to measure the chromaticity coordinates for the current illumination. In that regard, memory 161 may store CIE tristimulus functions $\bar{z}(\lambda)$, $\bar{y}(\lambda)$, and $\bar{x}(\lambda)$ as illustrated in FIG. 4. Controller 160 may then retrieve these functions and determine the corresponding CIE primaries $\bar{X}$, $\bar{Y}$, and $\bar{Z}$ by numerically integrating the following equations:

$$\bar{X} = \int R'(\lambda) \bar{x}(\lambda) d\lambda$$

$$\bar{Y} = \int R'(\lambda) \bar{y}(\lambda) d\lambda$$

$$\bar{Z} = \int R'(\lambda) \bar{z}(\lambda) d\lambda$$

where R'( ) is the spectral radiometric function discussed above. Given the CIE primaries, controller 160 may then calculate the x and y CIE chromaticity coordinates according to the following equations:

$$x=\overline{X}/(\overline{X}+\overline{Y}+\overline{Z})$$

$$y=\overline{Y}/(\overline{X}+\overline{Y}+\overline{Z})$$

Controller 160 may thus monitor the chromaticity values and tune the various color source intensities accordingly to achieve a desired effect. For example, controller 160 may adjust color rendering or contrast in this fashion.

Although illuminator 100 has been discussed with regard to three independent color sources, it will be appreciated that white light illumination can be achieved with just two sources. Conversely, rather than just use a RGB combination as discussed above, a greater number of color channels may used such as four, five, or more color channels may be implemented. In addition, the spectral content of the combined light may be characterized using a color camera instead of a spectroradiometer.

Embodiments described above illustrate but do not limit the invention. It should also be understood that numerous modifications and variations are possible in accordance with the principles of the present invention. Accordingly, the scope of the invention is defined only by the following claims.

We claim:

1. An ophthalmic illuminator, comprising:
   a plurality of color sources, each color source producing a light of a corresponding color;
   a combiner for combining the light from the color sources to produce a combined light;
   at least one optical fiber configured to receive the combined light and propagate the received combined light towards a distal end of the ophthalmic illuminator; and
   a controller configured to control an intensity for each of the color sources responsive to a sampling of a spectral content for the combined light by:
      constructing a spectral radiometric function that corresponds to the sampling of the spectral content;
      calculating an aphakically weighted radiometric quantity from the spectral radiometric function and an aphakic hazard function; and
      control the intensity for each of the color sources using the aphakically weighted radiometric quantity.

2. The ophthalmic illuminator of claim 1, further comprising a spectroradiometer for sampling the spectral content for the combined light.

3. The ophthalmic illuminator of claim 1, further comprising a color camera for sampling the spectral content for the combined light.

4. The ophthalmic illuminator of claim 1, further comprising a plurality of variable power amplifiers corresponding to the plurality of light sources such that each light source receives power from a corresponding one of the variable power amplifiers, and wherein the controller controls the intensity for each of the color sources by controlling a gain for the corresponding variable power amplifier.

5. The ophthalmic illuminator of claim 4, wherein each variable power amplifier comprises a variable current amplifier.

6. The ophthalmic illuminator of claim 1, further comprising a plurality of pulse width modulators corresponding to the plurality of color sources such that each pulse width modulator drives a corresponding one of the color sources, and wherein the controller controls a time-averaged intensity for each of the color source by controlling a pulse width modulation for the corresponding pulse width modulator.

7. The ophthalmic illuminator of claim 1, further comprising an RFID tag associated with the at least one optical fiber, wherein the controller controls the intensity of each color source responsive to data stored in the RFID tag.

8. The ophthalmic illuminator of claim 1, the controller configured to calculate the aphakically weighted radiometric quantity by intergrating a product of the spectral radiometric function with the aphakic hazard function.

9. The ophthalmic illuminator of claim 8, wherein the controller is further configured to estimate an aphakic exposure from the aphakically weighted radiometric quantity.

10. The ophthalmic illuminator of claim 9, wherein the controller is configured to control the intensity for each of the color sources using the aphakically weighted radiometric quantity by reducing aphakic hazard if the aphakic exposure exceeds a desired level.

11. A method of controlling ophthalmic illumination, comprising:
    producing a plurality of lights of different colors;
    combining the plurality of lights of different colors to produce a combined light;
    illuminating an operating field within a human eye with the combined light;
    measuring a spectral radiometric function for the combined light during the illumination;
    calculating an aphakically weighted radiometric quantity from the spectral radiometric function and an aphakic hazard function; and
    responsive to the measurement, adjusting an intensity for at least one of the lights of different colors according to the aphakically weighted radiometric quantity.

12. The method of claim 11, wherein measuring the spectral radiometric function for the combined light uses a spectroradiometer.

13. The method of claim 11, wherein measuring the spectral radiometric function for the combined light uses a color camera.

14. The method of claim 11, wherein the intensity is adjusted to increase color contrast of one or more retinal tissues.

15. The method of claim 11, wherein the intensity is adjusted to reduce an aphakic hazard to the retina.

16. An ophthalmic illuminator, comprising:
    a red LED;
    a green LED;
    a blue LED;
    a combiner for combining light from the LEDs to produce a combined light;
    at least one optical fiber configured to receive the combined light and propagate the received combined light towards a distal end of the ophthalmic illuminator; and
    a controller configured to control an intensity for each of the LEDs in response to a sampling of a spectral content for the combined light by:
       constructing a spectral radiometric function that corresponds to the sampling of the spectral content;
       calculating an aphakically weighted radiometric quantity from the spectral radiometric function and an aphakic hazard function; and
       controlling the intensity for each of the color sources using the aphakically weighted radiometric quantity.

17. The ophthalmic illuminator of claim 16, wherein the combiner comprises a Phillips prism.

18. The ophthalmic illuminator of claim 16, wherein the controller is further configured to control the intensity for each of the LEDs in response to an estimated irradiance based upon an estimate of a separation between the distal end of the ophthalmic illuminator and a retina.

19. The ophthalmic illuminator of claim 18, wherein the controller is further configured to control the intensity for each of the LEDs in response to an estimate of a duration of an ophthalmic illumination by the illuminator.

* * * * *